United States Patent [19]

Moriuchi et al.

[11] Patent Number: 5,092,561
[45] Date of Patent: Mar. 3, 1992

[54] TUBULAR BODY, METHOD OF MAKING TUBULAR BODY, AND FLOW CONTROL DEVICE HAVING TUBULAR BODY

[75] Inventors: Yousuke Moriuchi; Fumihisa Hirose, both of Fuji; Goichi Takei, Ueda, all of Japan

[73] Assignee: Terumo Kabushiki Kaisha, Tokyo, Japan

[21] Appl. No.: 409,014

[22] Filed: Sep. 18, 1989

[30] Foreign Application Priority Data

Sep. 22, 1988 [JP] Japan .................. 63-239149

[51] Int. Cl.$^5$ ........................... F16K 51/00
[52] U.S. Cl. ........................... 251/117; 251/342
[58] Field of Search ............ 137/599.1; 251/117, 251/331, 342; 138/40, 44, 45

[56] References Cited

U.S. PATENT DOCUMENTS

| | | |
|---|---|---|
| 2,516,029 | 7/1950 | Swindin ............... 138/45 X |
| 2,948,300 | 8/1960 | Fraser ..................... 138/45 |
| 4,192,303 | 3/1980 | Young et al. . |
| 4,291,702 | 9/1981 | Cole . |
| 4,341,224 | 7/1982 | Stevens . |
| 4,464,179 | 8/1984 | Barger et al. . |
| 4,624,662 | 11/1986 | Le . |
| 4,718,634 | 1/1988 | Bond ................... 251/342 X |
| 4,739,770 | 4/1988 | Stephens et al. ............... 251/331 X |
| 4,743,235 | 5/1988 | Waldbillig . |
| 4,802,650 | 2/1989 | Stricker ................. 251/117 |

FOREIGN PATENT DOCUMENTS

56-8033  1/1981  Japan .
60-207638 10/1985 Japan .
61-28624  8/1986  Japan .

Primary Examiner—Stephen M. Hepperle
Attorney, Agent, or Firm—Frishauf, Holtz, Goodman & Woodward

[57] ABSTRACT

A tubular body for reducing the rate at which a fluid flows to a predetermined rate with a resistance in a flow control device of a pressure measuring system, includes a tubular member having an axis along which the fluid can flow therethrough, and a land projecting radially inwardly from an inner wall surface of the tubular member. The tubular member and the land are integrally formed as a unitary structure, the land having an orifice extending along the axis of the tubular member. A method of manufacturing the tubular body, and a flow control device incorporating the tubular body are also disclosed.

18 Claims, 11 Drawing Sheets

TUBULAR BODY, METHOD OF MAKING TUBULAR BODY, AND FLOW CONTROL DEVICE HAVING TUBULAR BODY

BACKGROUND OF THE INVENTION

The present invention relates to a tubular body for controlling the flow rate of a fluid such as a fluid transfused into a human body in a measuring system for measuring the blood pressure, for example, a method of making such a tubular body, and a flow control device incorporating such a tubular body, and more particularly to a tubular body which can provide a flow passage capable of allowing a fluid to flow at a relatively high rate therethrough in order to fill the fluid in the measuring system before starting to measure the blood pressure, which can provide a flow passage capable of limiting the flow of the fluid to a lower rate for pressure transmission while the blood pressure is being measured, which prevents air from remaining in the flow passage when it is defined to provide a high flow rate, so that it permits the blood pressure to be transmitted accurately, and which is simple in structure, small in size, and can be manufactured at a lower cost, a method of manufacturing such a tubular body, and a flow control device incorporating such a tubular body.

There have recently been developed blood pressure measuring systems for monitoring the blood pressure of patients continuously with time. Such blood pressure measuring systems are widely employed in medical applications.

A blood pressure measuring system generally comprises a fluid bag for supplying the system with a fluid to be transfused such as physiological saline, a catheter to be inserted into the body of a patient where the blood pressure is to be measured, a pressure transducer for detecting the blood pressure through the fluid filled in the system, and a display/recorder for displaying and recording the value of the blood pressure which is produced by the pressure transducer.

To measure the blood pressure of a patient, the catheter is inserted into an artery of the patient, and is then supplied with the fluid such as physiological saline from the fluid back at a very low rate By supplying the fluid to the catheter, the blood is prevented from flowing into the catheter and hence from being solidified. A change in the pressure of the fluid in the catheter is detected by the pressure transducer, and its value is fed to the display/recorder. As a result, the blood pressure condition of the patient can be monitored on a real-time basis.

In order to control the fluid to flow at a desired rate, a flow control device having a flow resistor is disposed in the tube by which the fluid bag and the catheter are interconnected. The fluid is controlled to flow at a low rate by the flow resistor.

To use the catheter on a human body, it must first be flushed with a fluid to be transfused by a process known as priming so that any air remaining in the catheter and the tube connected thereto will completely be removed. Various flow control devices have been proposed which have mechanisms for temporarily increasing the flow rate of a fluid so that the catheter can be primed within a short period of time. See, for example, U.S. Pat. Nos. 4,192,303 and 4,464,179, Japanese Utility Model Publication No. 61(1986)-28624, Japanese Patent Publication No. (1985) 60-57336 Japanese Laid-Open Patent Publications Nos. 56(1981)-8033, and 60(1985)-207638, and U.S. Pat. No. 4,624,662. The disclosed flow control devices are however complex in construction, made up of many components, and expensive to manufacture. They cannot completely be de-aired, and therefore the blood pressure to be measured is prevented from being transmitted accurately because of remaining air in the system. As a result, the measured blood pressure values are subject to errors.

In view of the above drawbacks, the applicant has proposed flow control devices which are simple in structure and have a good de-airing capability, as disclosed in Japanese Laid-Open Patent Publications Nos. 1(1989)-135970 and 1(1989)-160529.

The disclosed flow control devices include a closure member having a first land, and a tubular body having a second land and fitted over the closure member.

For priming these flow control devices, the closure member is manually deformed elastically to space the first and second lands from each other, thus defining a flushing passage therebetween which allows a fluid to flow at a high rate. The fluid can thus be filled into a pressure transmitting system from the flushing passage within a short period of time. For measuring the blood pressure of a patient, the closure member is released of the manual push to close the flushing passage. The fluid is then controlled to flow at a low rate by the resistance produced by an orifice defined through the second land of the tubular body.

SUMMARY OF THE INVENTION

It is a major object of the present invention to provide a tubular body which can effectively de-air, or remove air bubbles from, a pressure transmitting system when the pressure transmitting system is to be filled by prim in at a high rate with a fluid that is to be transfused, and which is simple in structure, can efficiently be manufactured, and is easy to handle, a method of manufacturing such a tubular body, and a flow control device which incorporates such a tubular body.

Another object of the present invention is to provide a tubular body for reducing the rate at which a fluid flows to a predetermined rate with a resistance in a flow control device of a pressure measuring system, said tubular body comprising a tubular member having an axis along which the fluid can flow therethrough, and a land projecting radially inwardly from an inner wall surface of said tubular member, said tubular member and said land being integrally formed as a unitary structure, said land having an orifice extending along said axis.

Still another object of the present invention is to provide the tubular body wherein said tubular member has inlet and outlet passages defined therein and spaced along said axis, said land having two slanted surfaces converging toward each other from said inlet and outlet passages, said orifice opening at said slanted surfaces.

Yet another object of the present invention is to provide the tubular body wherein said land has a flat surface at converging ends of said slanted surfaces, said flat surface partly defining a flushing passage through said tubular member.

Yet still another object of the present invention is to provide the tubular body wherein each of said slanted surfaces is inclined to said axis at an angle which ranges from about 5° to about 70°.

A further object of the present invention is to provide the tubular body wherein said angle ranges from about 10° to about 45°.

A still further object of the present invention is to provide the tubular body wherein said angle is about 18°.

A yet further object of the present invention is to provide the tubular body wherein said tubular member and said land are made of a hard synthetic resin.

A yet still further object of the present invention is to provide the tubular body wherein said hard synthetic resin is polycarbonate.

It is also an object of the present invention to provide a method of manufacturing a tubular body for reducing the rate at which a fluid flows to a predetermined rate with a resistance in a flow control device of a pressure measuring system said method comprising the steps of defining a mold cavity for molding the tubular body with a first mold, a second mold, and at least one core pin, placing a filamentary element through said core pin as a first core pin, and one of said first mold, said second mold, and another core pin as a second core pin, pouring a molten material into said mold cavity, solidifying the molten material as a tubular body product in said mold cavity, and removing said filamentary element from the solidified tubular body product, leaving an orifice in the tubular body product.

Another object of the present invention is to provide the method further including the step of keeping said filamentary element taut between said first and second core pins disposed between said first and second molds.

Still another object of the present invention is to provide the method further including the step of keeping said filamentary element taut between said first core pin and said first mold as a movable mold.

Yet another object of the present invention is to provide the method further including the step of keeping said filamentary element taut between said first core pin and said second mold as a fixed mold.

Yet still another object of the present invention is to provide the method further including the steps of spacing said first and second molds away from each other, removing said core pins, said filamentary element and said tubular body product together, and removing said filamentary element from the tubular body product.

A further object of the present invention is to provide the method wherein said filamentary element comprises a wire.

A yet further object of the present invention is to provide a flow control device for use in a pressure measuring system, comprising a tubular body having an inlet passage and an outlet passage which are spaced from each other along an axis thereof, and including a first land having an orifice defined therein and providing communication between said inlet and outlet passages at all times, and an elastically deformable closure member having a second land normally held against said first land, whereby said closure member can be elastically deformed to space at least a portion of said second land from said first land to define therebetween a flow passage for allowing a fluid to pass at a relatively high rate.

A still further object of the present invention is to provide the flow control device wherein said first land projects inwardly from a side wall of said tubular body, said closure member being fitted over said tubular body, said second land projecting into said tubular body and being movable into and out of contact with said first land, whereby said closure member can be elastically deformed to communicate between said inlet and outlet passages through said flow passage.

Another object of the present invention is to provide the flow control device wherein said closure member has a pull knob projecting away from said second land.

Still another object of the present invention is to provide the flow control device wherein said second land has slanted surfaces converging toward each other from said inlet and outlet passages.

Yet another object of the present invention is to provide the flow control device wherein said second land has a flat surface at converging ends of said slanted surfaces, said flat surface being normally held against a flat surface of said first land to close said flow passage.

Yet still another object of the present invention is to provide the flow control device wherein said flat surface of said second land is harder than the rest of the second land.

A further object of the present invention is to provide the flow control device further including a hard member having said flat surface and mounted on said second land.

A still further object of the present invention is to provide the flow control device wherein each of said slanted surfaces is inclined to said axis at an angle which ranges from about 5° to about 70°.

A yet further object of the present invention is to provide the flow control device wherein said angle ranges from about 10° to about 45°.

A yet still further object of the present invention is to provide the flow control device wherein said angle is about 24.

Another object of the present invention is to provide the flow control device wherein said closure member is made of an elastomeric material.

Still another object of the present invention is to provide the flow control device wherein said elastomeric material is silicone rubber.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Like or corresponding parts are denoted by like or corresponding reference numerals throughout views.

Figure 1:
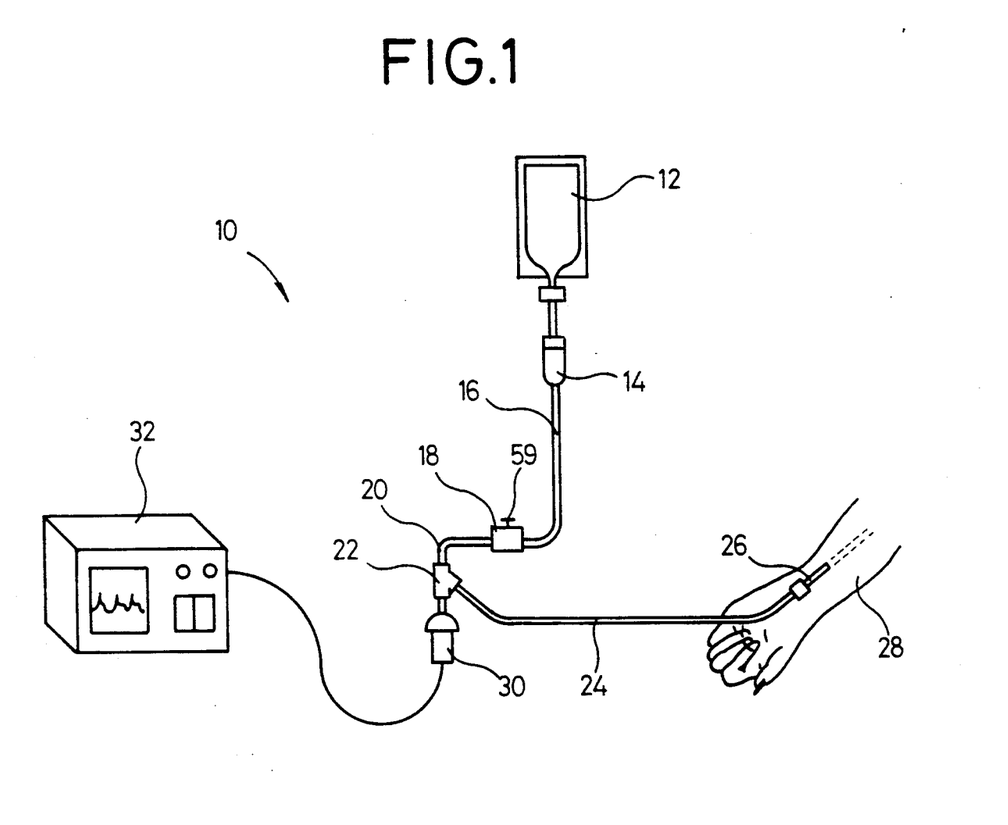
FIG. 1 is a schematic view showing a blood pressure measuring system incorporating a flow control device according to the present invention.

FIG. 1 shows a blood pressure measuring system, generally denoted at 10, which employs a flow control device 18 according to the present invention. The blood pressure measuring system 10 includes a fluid bag 12 filled with a fluid to be transfused such as physiological saline, and a dripping tube 14 connected to and positioned below the fluid bag 12. The fluid bag 12 and the dripping tube 14 are sup ported on a stand (not shown). The dripping tube 14 is connected to the flow control device 18 through a tube 16. The flow control device 18 has its downstream port joined to a tube joint 22 through a tube 20. The tube joint 22 is branched into two members, one connected by a tube 24 to a catheter 26 to be inserted into a blood vessel of a patient 28, and the other connected to a pressure transducer 30. The pressure transducer 30 is electrically connected to a display/recorder 32.

The flow control device 18 will be described in greater detail with reference to FIGS. 2 and 3.

Figure 2:
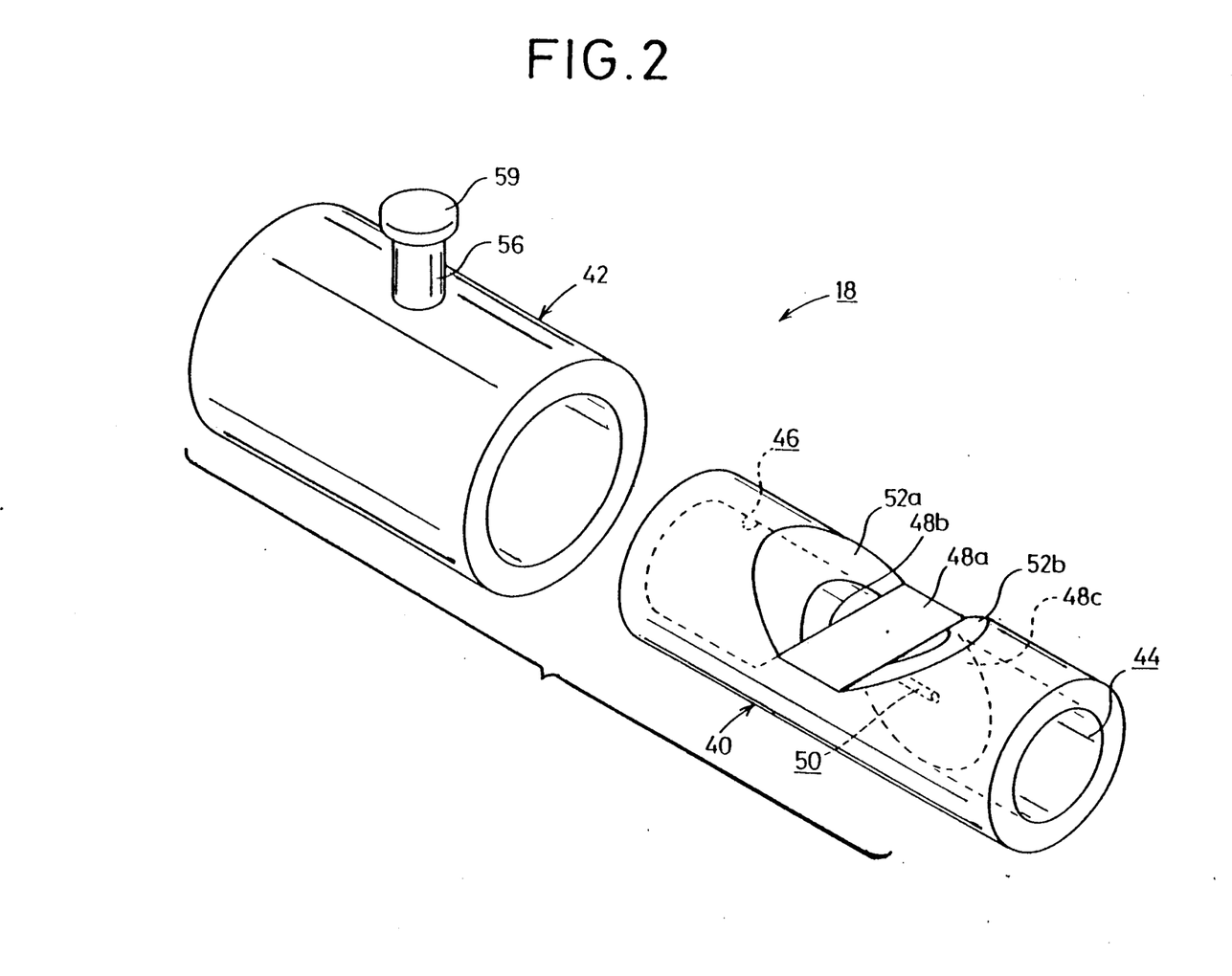
FIG. 2 is an exploded perspective view of the flow control device which includes a tubular body according to the present invention.
Figure 3:
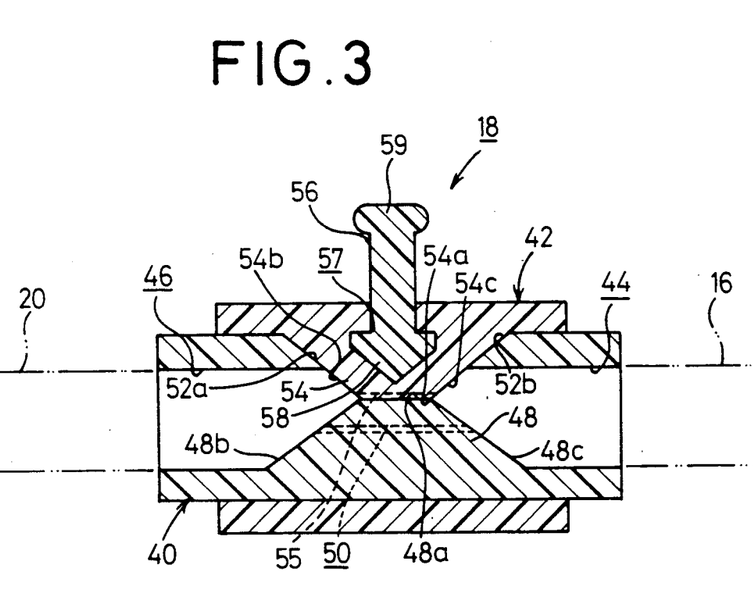
FIG. 3 is a longitudinal cross-sectional view of the tubular body.

As shown in FIG. 2, the flow control device 18 basically comprises a tubular body 40 and a tube 42 fitted over the tubular body 40 and closing a portion of a flow passage defined in the tubular body 40.

The tubular body 40 is of a substantially cylindrical unitary structure made of a relatively hard synthetic resin such as polycarbonate or the like. As shown in FIG. 3, the tubular body 40 has an inlet passage 44 and an outlet passage 46 which are defined therein and held in communication with each other in the center of the tubular body 40. The tubular body 40 has a first land 48 disposed centrally therein and projecting inwardly from a tubular member thereof. The first land 48 has a trapezoidal vertical cross-sectional shape such that the first land 48 extends partly into the inlet and outlet passages 44, 46. The first land 48 has a flat surface 48a on its top and a pair of slanted surfaces 48b, 48c spreading from the fat surface 48a and inclined with respect to the axis of the tubular body 40.

The first land 48 has a central narrow orifice 50 defined therethrough and extending axially with respect to the tubular body 40. The orifice 50 has a diameter ranging from 0.02 mm to 0.1 mm, for example. The orifice 50 provides communication between the inlet and outlet passages 44, 46.

The tubular body 40 has a central side opening defined in a side wall thereof in confronting relation to the first land 48, the central side opening being defined by a pair of slanted surfaces 52a, 52b converging toward the flat surface 48a of the first land 48. The orifice 50 opens at the slanted surfaces 52a, 52b. The tube 42 has a second land 54 serving as a closure portion and fitted in the central side opening of the tubular body 40. The central side opening has a shape complementary to the second land 54.

The tubular body 40 are dimensioned as follows: The tubular body 40 has an outside diameter of 6.0 mm, an inside diameter of 3.0 mm, and a length of 21.0 mm. The first land 48 has a height of 2.5 mm, its flat surface 48a has a length of 2.0 mm in the axial direction of the tubular body 40, and each of the slanted surfaces 48b, 48c is inclined to the axis of the tubular body 40 at an angle which ranges from about 5° to about 70°, preferably from about 10° to about 45°, and more preferably is about 18°.

If the angle of the slanted surfaces 48b, 48c to the axis of the tubular body 40 were smaller than 5°, then the slanted surfaces 48b, 48c would be long, making the tubular body 40 long. If the angle were larger than 70°, then air would remain trapped at the base portions of the slanted surfaces 48b, 48c.

The tube 42, which serves as a closure member, is fitted over the tubular body 40. The tube 42 is made of an elastomeric material such as silicone rubber. The tube 42 is fitted over the tubular body 40 in fluidtight relation. The tube 42 has a length of 12.1 mm, an outside diameter of 9.0 mm, and an inside diameter which is slightly smaller than the outside diameter of the tubular body 40.

The second second land 54 projects from the tube 42 into the tubular body 40 and has a trapezoidal vertical cross-sectional shape complementary to the central side opening which is defined by the slanted surfaces 52a, 52b. The second land 54 has a flat surface 54a and a pair of slanted surfaces 54b, 54c similarly to the first land 48 of the tubular body 40. The slanted surfaces 54b, 54c spread upwardly in the vertical cross section of the second land 54. Normally, the flat surface 54a is pressed against the flat surface 48a of the first land 48, with the result that the inlet and outlet passages 44, 46 are substantially held out of communication with each other except through the orifice 50. When the second land 54 is pressed against the first land 48, the second land 54 has a height of 2.0 mm, its flat surface 54a has a length of 2.0 mm in the axial direction of the tube 42, and each of the slanted surfaces 54b, 54c is inclined to the axis of the tube 42 at an angle which ranges from about 5° to about 70°, preferably is about 24°.

The tube 42 made of an elastomeric material is so elastically deformable that it is easily flexible when a pull knob 56 (described later) joined thereto is pulled up. The flat surface 54a of the second land 54 should preferably be harder than the rest of the second land 54, so that the flat surface 54a will intimately contact the flat surface 48a of the tubular body 40 which is made of a hard synthetic resin. It is also possible to construct the flat surface 54a by attaching a separate member 55 of a hard material to the distal end of the second land 54 as indicated by the broken line.

The pull knob 56 which is shaped as a rod is joined to the tube 42. The pull knob 56 is pulled up to elastically deform the tube 42. More specifically, the tube 42 has a top-shaped space 57 defined centrally therein, and the pull knob 56 has a complementarily shaped larger-diameter distal end 58 either fitted in or securely mounted in the space 57 by adhesive bonding. The pull knob 56 has on its opposite end a disc-shaped grip 59 having its outer edge projecting radially outwardly. The pull knob 56 projects in a direction away from the second land 54 so that when the pull knob 56 is pulled up, it elastically deforms the tube 42 to easily define a flushing path.

A process for manufacturing the tubular body 40 will be described with reference to FIGS. 4 through 7.

Figure 4:
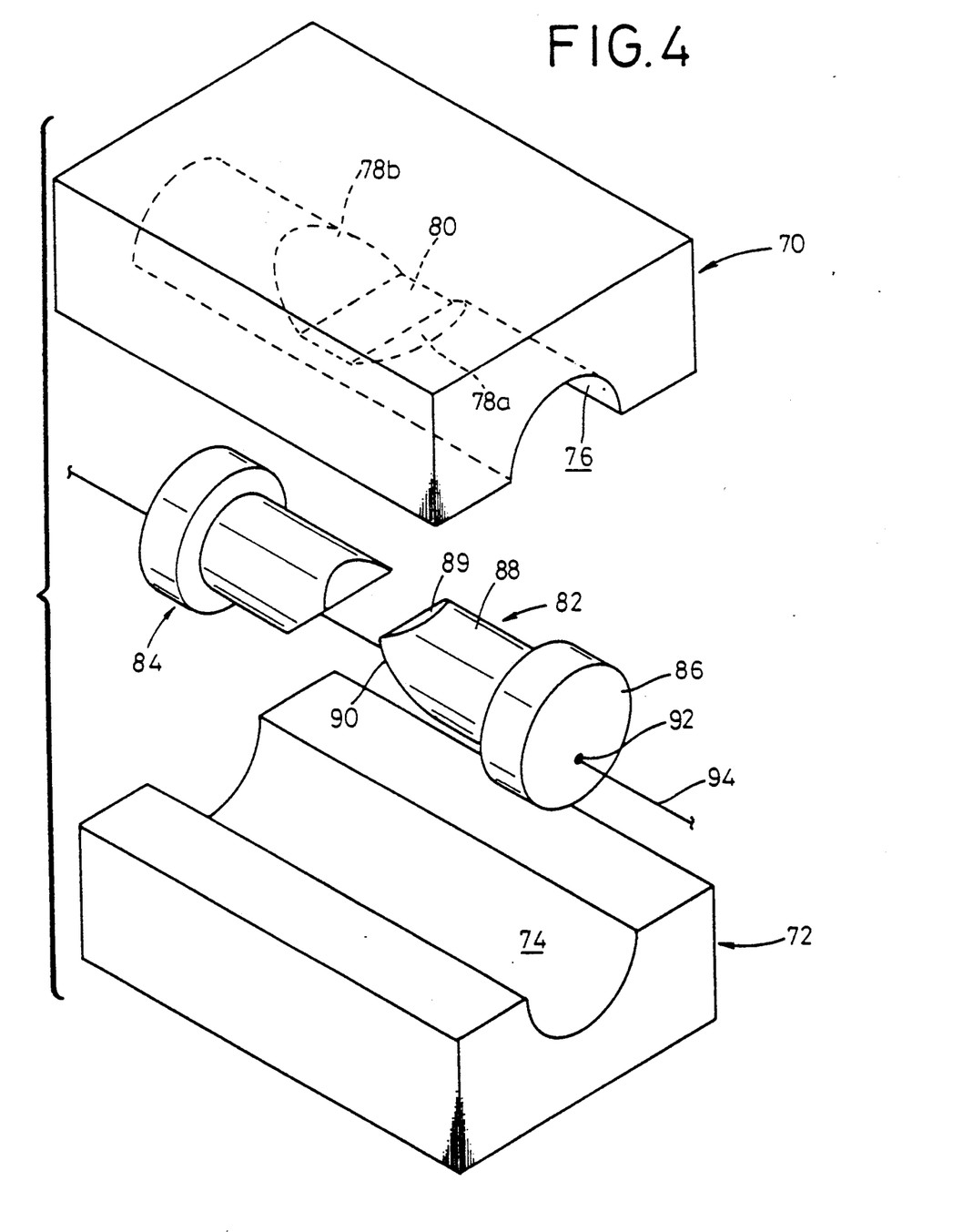
FIG. 4 is an exploded perspective view of a mold mechanism for molding the tubular body.

The tubular body 40 is molded by injection molding because the injection molding process is high in production efficiency and ensures uniform product quality. To mold the tubular body 40, there is employed a mold mechanism comprising an upper mold 70 and a lower mold 72 as shown in FIG. 4. The upper mold 70 is movable and the lower mold 72 is fixed. However, the upper mold 70 may be a movable mold and the lower mold may be a movable mold. The lower mold 72 has a semicylindrical recess 74 defined centrally in and extending longitudinally along the upper surface thereof Likewise, the upper mold 70 has a semicylindrical recess 76 defined centrally in and extending longitudinally in the lower surface thereof. The recess 76 of the upper mold 70 has a pair of slanted surfaces 78a, 78b extending downwardly toward each other and terminating at a flat surface 80 which faces downwardly.

When the upper and lower molds 70, 72 are put together, their recesses 76, 74 jointly define a cylindrical hole in which a pair of side core pins 82, 84 is slidably flange 86 and a cylindrical member 88 extending axially from the flange 86 and having two slanted surfaces 89, 90 remote from the flange 86. The slanted surfaces 89, 90 extend toward each other and have their ends joined to each other. The side core pin 82 has a narrow hole 92 defined axially through the flange 86 and the cylindrical member 88, with a thin wire 94 of metal extending through the hoe 92. The other side core pin 84 is of the same construction as that of the side core pin 82. The wire 94 may be of a heat-resistant synthetic resin rather than metal.

Figure 5:
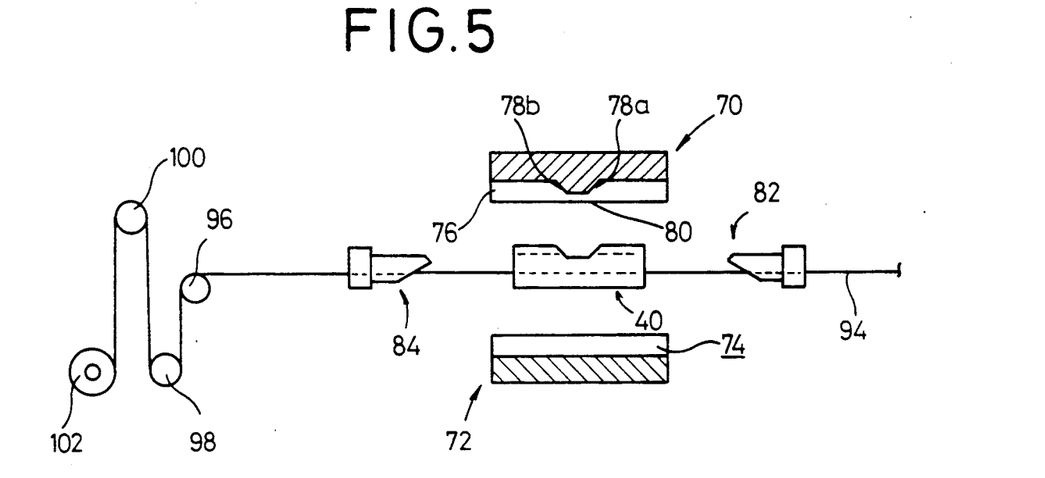
FIG. 5 is a schematic view showing the relationship between the mold mechanism, a wire, and a takeup reel.

The wire 94 extends through the hole 92 in the side core pin 82 and also through the similar hole in the side core pin 84. As shown in FIG. 5, the wire 92 is trained around first through third rollers 96, 98, 100, and wound around a takeup reel 102. Using the mold mechanism constructed above, the tubular body 40 is manufactured as described below.

Figure 6:
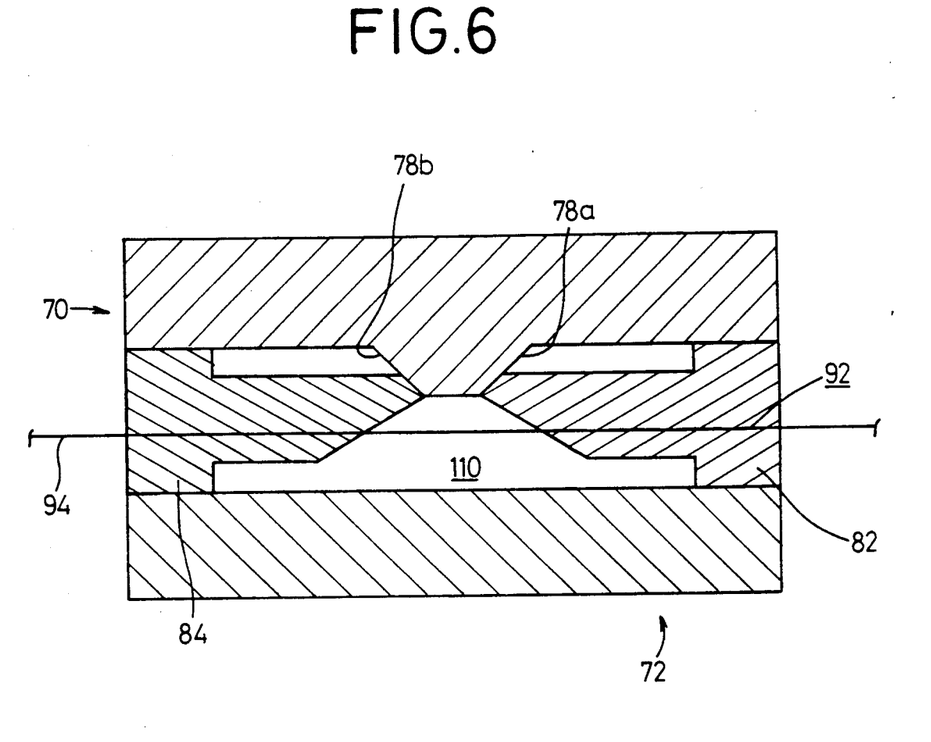
FIG. 6 is a longitudinal cross-sectional view of the mold mechanism.

The movable upper mold 70 is joined to the fixed lower mold 72, and then an actuator (not shown) is operated to insert the side core pins 82, 84 into the cylindrical hole which is defined jointly by the semicylindrical recesses 76, 74. At this time, the wire 94 has been inserted through the holes extending axially through the side core pins 82, 84. As a result, the mold mechanism as shown in FIG. 6 is set up. The upper mold 70, the lower mold 72, the side core pins 82, 84, and the wire 94 jointly define a mold cavity 110 which is complementary in shape to the tubular body 40 shown in FIG. 2. Then, a molten material is poured into the mold cavity 110 through a runner (not shown). When the molten material has been solidified after elapse of a certain period of time, the tubular body 40 is produced by the mold mechanism.

Figure 7:
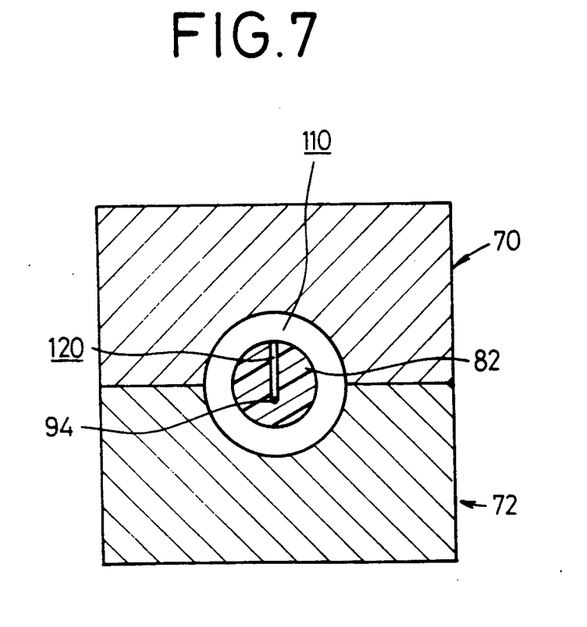
FIG. 7 is a transverse cross-sectional view of the mold mechanism.

To open the mold mechanism, the upper mod 70 is first moved away from the lower mold 72, and then the side core pins 82, 84 are retracted. A rotative drive source (not shown) coupled to the takeup reel 102 is energized to rotate the takeup reel 102 in a direction to wind the wire 94. The wire 94 is withdrawn from the side core pins 82, 84, travels around the rollers 96, 98, 100, and is wound around the takeup reel 102. As shown in FIG. 7, the side core pins 82, 84 may have respective slits 120 opening toward the upper mold 70, and the wire 94 may be inserted into the slits 120. The slits 120 may be defined by a wire cutting machining process. With the slits 120 defined, the process of inserting the wires 94 through the holes in the side core pins 82, 84, and the rollers 96, 98, 100 and the takeup reel 102 may be dispensed with. A slit 120 may be defined in only one of the side core pins 82, 84. In this connection, the wire 94 has a diameter of about 50 $\mu$m and an air pressure is present in the slits 120. Therefore, the molten material is substantially prevented from entering the slits 120 and hence from forming burrs on the produced tubular body 40. If any burrs are formed on the tubular body 40, they can be removed by smoothing the inner peripheral surface of the tubular body 40 after it has been molded.

The tubular body 40, the method of making the tubular body 40, and the flow control device 18 which incorporates the tubular body 40 are essentially constructed as described above. Their operation and advantages will now be described below.

In FIG. 1, the dripping tube 14 and the flow control device 18 are interconnected by the tube 16, and the outlet port of the flow control device 18 and the tube joint 22 are interconnected by the tube 20. One of the branch members of the tube joint 22 is connected to the catheter 26 through the tube 24, and the other branch member is connected to the pressure transducer 30. After the components of the blood pressure measuring system 10 have been connected, the fluid bag 12 filled with a fluid to be transfused such as physiological saline and the dripping tube 14 are held at a certain height on the stand (not shown). As a result, the sum of the head of the fluid developed by the height of the dripping tube 14 and the pressure of a pressurizing cuff which pressurizes the fluid bag 12 is applied as a differential pressure across the flow control device 18.

Before the blood pressure of a patient is measured by the blood pressure measuring system 10, the blood pressure measuring system 10 is primed so that the tubes thereof are filled with the physiological saline.

Figure 8:
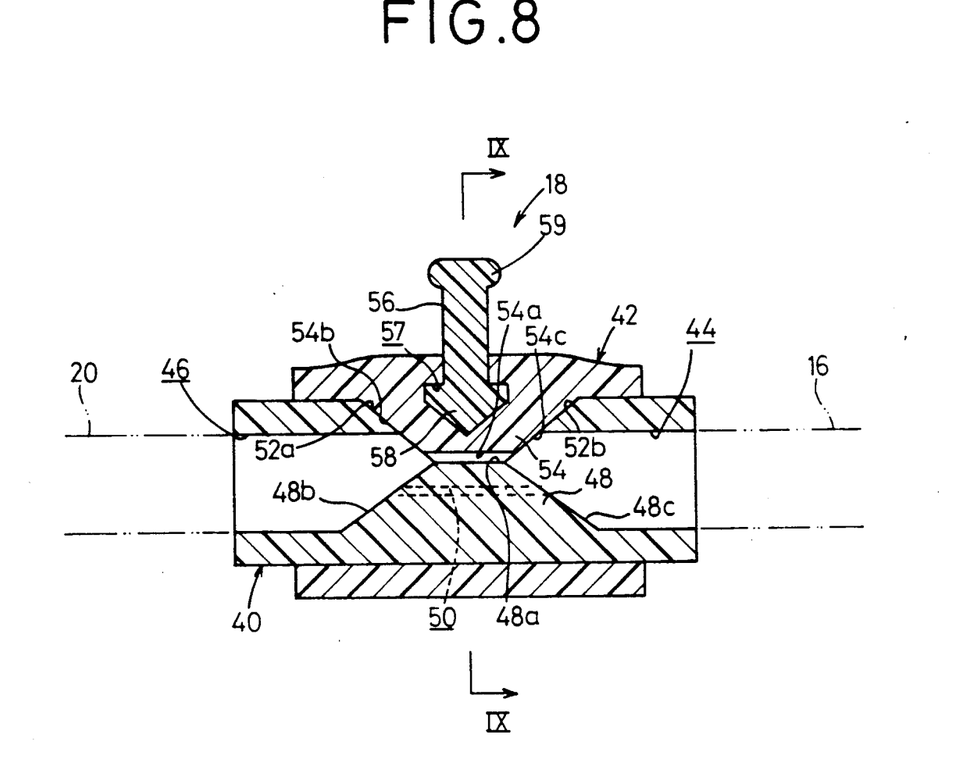
FIG. 8 is a longitudinal cross-sectional view of the flow control when it is primed.
Figure 9:
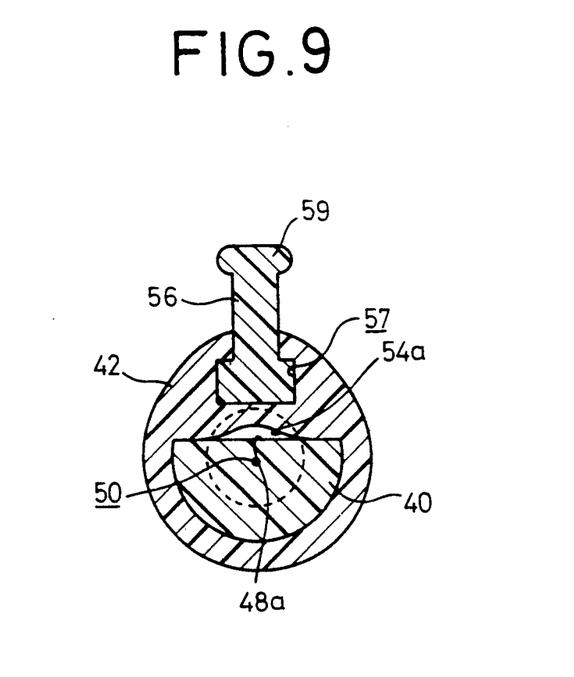
FIG. 9 is a transverse cross-sectional view taken along line IX—IX of FIG. 8.

In order to prime the blood pressure measuring system 10, the operator grips the grip 59 of the pull knob 56 with fingers, and pulls up the pull knob 56 against the resiliency of the tube 42 itself. As shown in FIGS. 8 and 9, the tube 42 is elastically deformed until the second land 54 of the tube 42 is lifted away from the first land 48 of the tubular body 40. Before this happens, the flat surface 48a of the first land 48 has been held against the flat surface 54a of the second land 54, thus substantially cutting off communication between the inlet and outlet passages 44, 46 except through the orifice 50. With the flat surface 54a displaced upwardly from the flat surface 48a, the inlet and outlet passages 44, 46 are brought into substantial communication with each other as shown in FIG. 8. Therefore, a flow passage is defined by the gap thus formed between the flat surfaces 48a, 54a and serving as a flushing passage. The physiological saline introduced from the tube 16 through the inlet passage 44 flows through the flushing passage at a rate much higher than possible if it flows through only the orifice 50. The physiological saline then flows into the tube 20 through the outlet passage 46. The tubes downstream of the tube 20 are thus filled with the supplied physiological saline in a short period of time. The slanted surface 48c of the first land 48 and the slanted surface 54c of the second land 54 are spread at a large angle from each other in the upstream direction of the flow of the physiological saline. Therefore, the physiological saline flows into the flushing passage while being subjected to as small a resistance as possible.

In the above embodiment, the flushing passage is defined within the diameter of the inlet and outlet passages 44, 46 and is oriented unidirectionally. The first and second lands 48, 54 are tapered by their slanted surfaces 48b, 48c and 54b, 54c, respectively, which extend toward each other or converge toward the axis of the tubular body 40. With such an arrangement, any air which remains trapped in the flow control device 18 during an initial stage of the priming process is effectively discharged out of the flow control device 18 without leaving any air bubbles therein. When the tube 42 is elastically deformed by the pull knob 56, the second land 54 is spaced from the first land 48 while the slanted surfaces 54b, 54c are sliding along the slanted surfaces 52a, 52b, respectively, of the tubular body 40. Consequently, air is not introduced into and does not remain in the opening which is defined by the slanted surfaces 52a, 52b and in which the second land 54 is fitted.

After the tubes of the blood pressure measuring system 10 has been filled with the physiological saline by the priming process, the pull knob 56 is released. The tube 42 elastically restores its initial configuration, and the flat surface 54a of the second land 54 is held against the flat surface 48a of the first land 48. Therefore, any flow passage effectively present in the flow control device 18 at this time is limited to a low-rate flow passage defined by only the orifice 50 extending through the first and 48. Inasmuch the flat surface 54a of the second land 54 is harder or provided by the hard member 55, it is effectively pressed closely against the flat surface 48a of the first land 48.

Then, the catheter 26 is inserted into a vein of the patient 28 for the measurement of the blood pressure. The physiological saline dripped from the fluid bag 12 into the dripping tube 14 flows from the dripping tube 14 through the tube 16 under the sum of the pressure developed by the pressurizing cuff and the head of the fluid developed by the height of the dripping tube 14. The physiological saline is then introduced from the inlet passage 44 into the flow control device 18. The physiological saline is controlled by the orifice 50 to flow at a low rate (which is 4.0 ml/hour when the differential pressure across the flow control device 18 is 300 mHg), through the tube 20, the tube joint 22, and the tube 24, and then into the blood of the patient 28 from the catheter 26. During this time, the blood pressure of the patient 28 is transmitted to the pressure transducer 30 through the physiological saline in the tube 24, which serves as a pressure transmitting medium. The pressure transducer 30 then generates a voltage proportional to the blood pressure, and applied to the voltage to the display/recorder 32. As a result, the measured value of the blood pressure of the patient 28 is displayed on the display/recorder 32 on a real-time basis.

Figure 10:
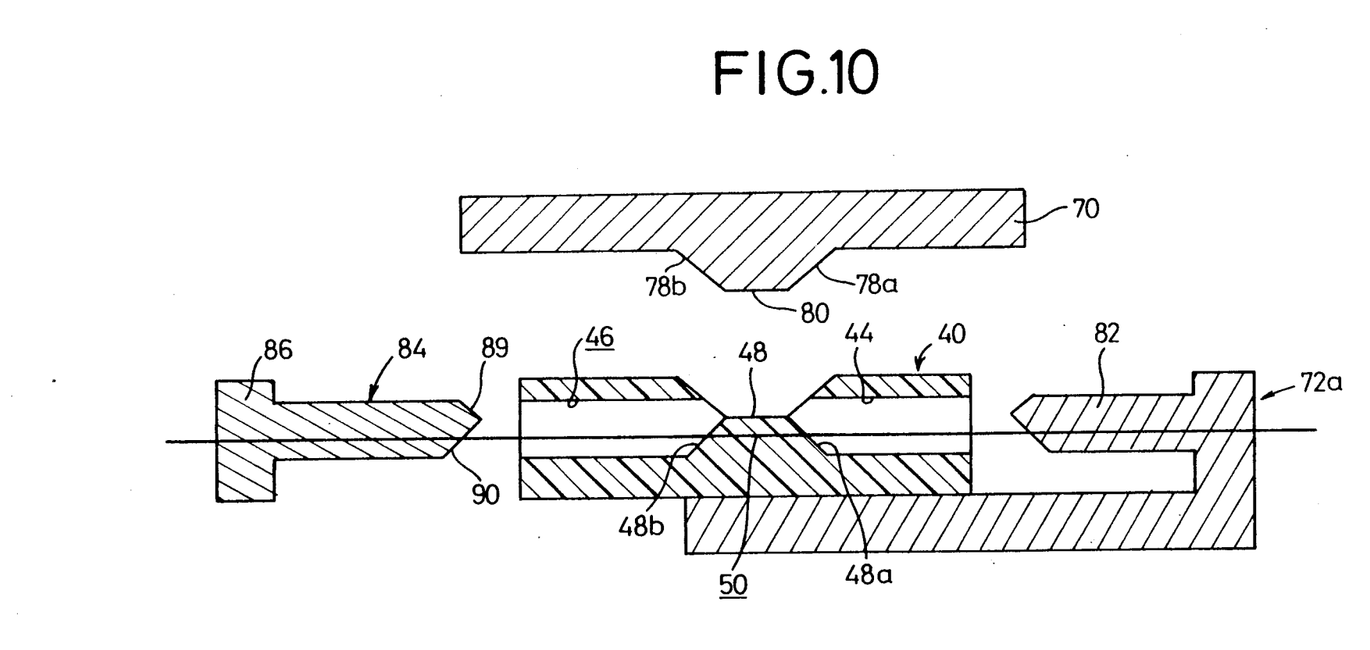
FIG. 10 is an exploded longitudinal cross-sectional view of a mold mechanism according to another embodiment of the present invention.

FIG. 10 shows a mold mechanism according to another embodiment of the present invention. In the preceding embodiment, the tubular body 40 is molded by the upper mold 70, the lower mold 72, the side core pins 82, 84, and the wire 94, which are separate from each other. In the embodiment shown in FIG. 10, a lower mold 72a comprises the lower mold 72 and the side core pin 82 which are integrally joined to each other. Thus, the side core pin 82 and the lower mold 72 are of a unitary construction.

When the mold mechanism is to be opened, the upper mold 70 is elevated, then the side core pin 84 is retracted, and thereafter the molded product is taken out by being moved in the same direction as that in which the side core pin 84 has been retracted. The mold mechanism shown in FIG. 10 is constructed of a smaller number of separate parts than the mold mechanism shown in FIGS. 4 and 6.

Figure 11:
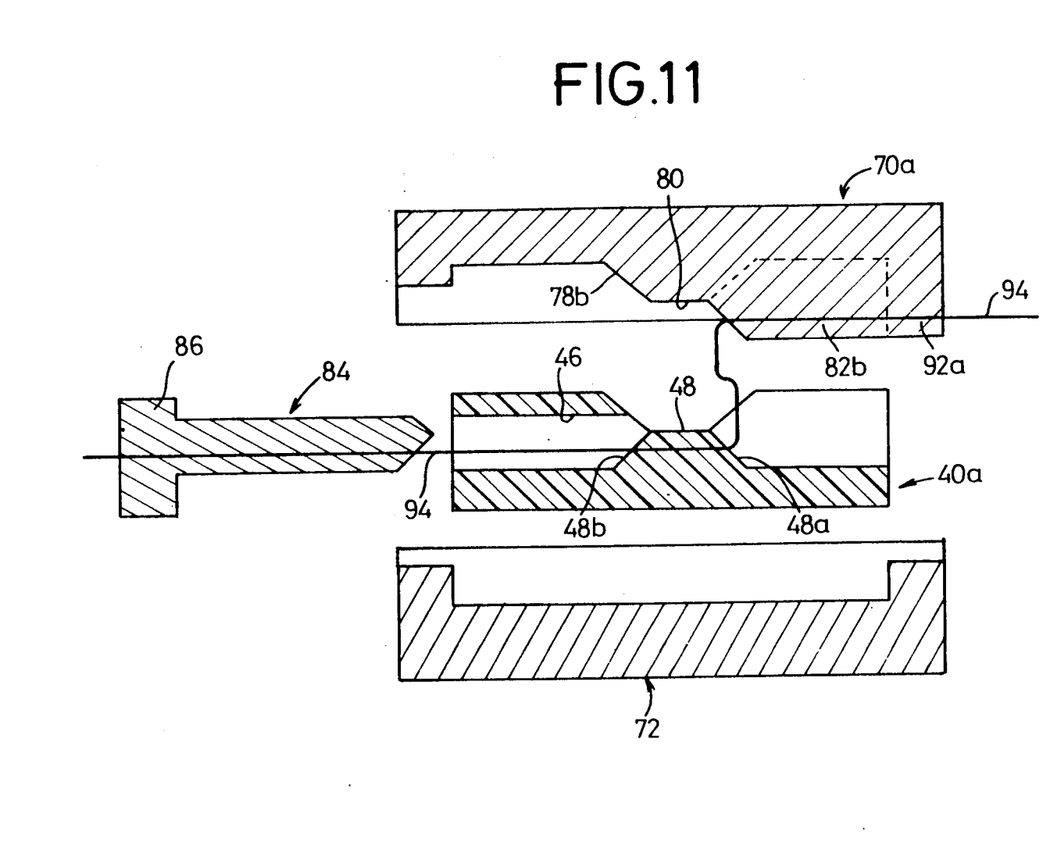
FIG. 11 is an exploded longitudinal cross-sectional view of a mode mechanism according to still another embodiment of the present invention.

A mold mechanism according to still another embodiment shown in FIG. 11 is also made up of a smaller number of separate parts. More specifically, an upper mod 70a comprises the upper mold 70 and the side core pin 82 which are integrally joined to each other. A fat thick portion 82b, corresponding to the side core pin 82, projects from the upper mold 70, and is positioned so as to enter the lower mold 72. The side core pin 84 is separately disposed in the space between the upper mold 70a and the lower mold 72.

Figure 12:
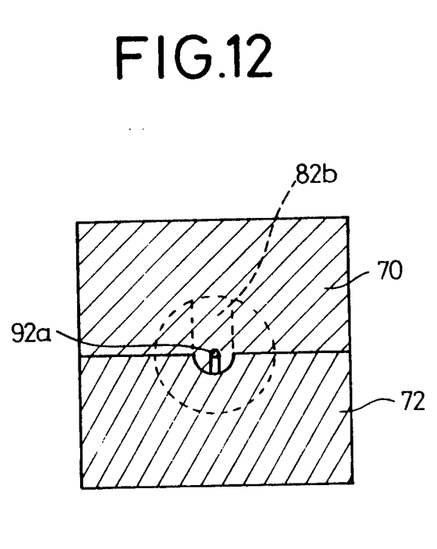
FIG. 12 is a transverse cross-sectional view of the mold mechanism shown in FIG. 11 when it is assembled.
Figure 13:
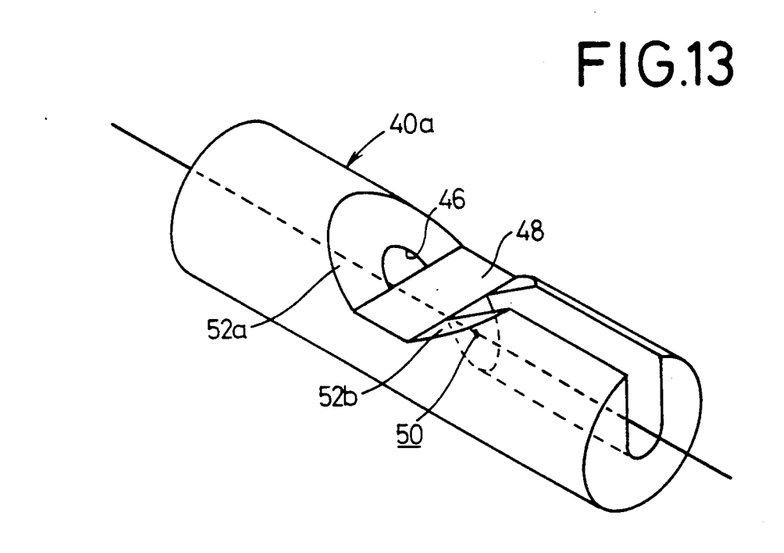
FIG. 13 is a perspective view of a tubular body which is molded by the mold mechanism shown in FIGS. 11 and 12.
Figure 14:
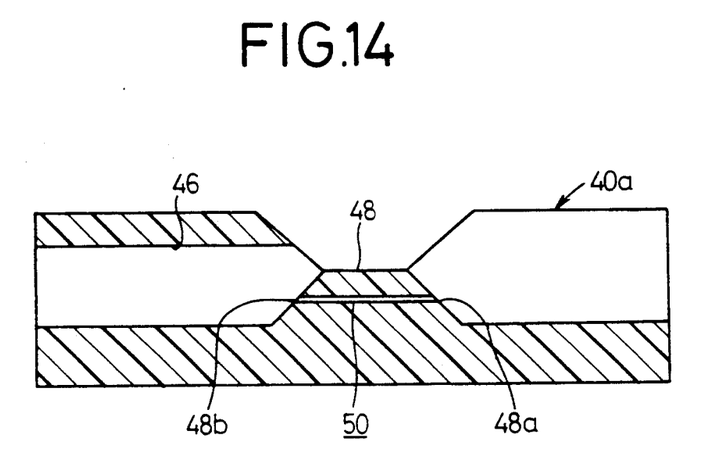
FIG. 14 is a longitudinal cross-sectional view of the tubular body illustrated in FIG. 13.
Figure 15:
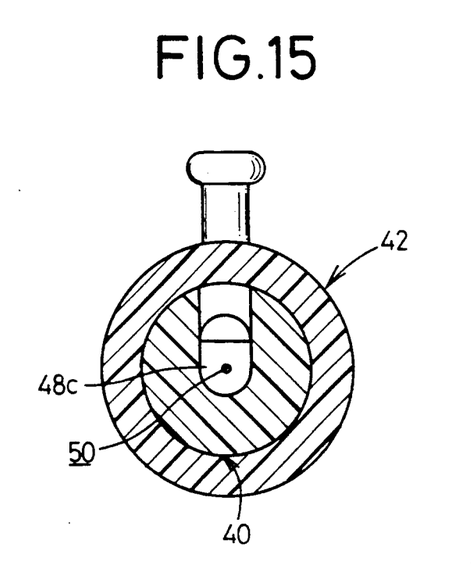
FIG. 15 is a transverse cross-sectional view of the tubular body shown in FIGS. 13 and 14 which is fitted in a tube.

A hole 92a (see also FIG. 12) is defined axially through the portion corresponding to the side core pin 82b, and the wire 94 is inserted through the hole 92a. In order to open the mold mechanism, the wire 94 is loosened, then the upper mold 70a is lifted, and thereafter the side core pin 84 is retracted, after which a molded tubular body 40a can be taken out.

Since the upper mold 70a includes the flat side core portion 82b, the molded tubular body 40a has a corresponding inlet passage 44a of a large volume which opens upwardly. The large inlet passage 44a however does not impair the function of the tubular body 40a because the tubular body 40a is surrounded by the tube 42.

With the present invention, as described above, an elastically deformable closure member has a land having a trapezoidal vertical cross section, and a tubular body has another land of a similar shape for abutment against the land of the closure member. The lands define tapered flow passages on their opposite sides which are directed toward a flushing passage. When the land of the closure member is spaced from the land of the tubular body by elastically deforming the closure member, the flushing passage which allows a fluid to flow at a high rate is opened from a inlet passage toward an outlet passage of the tubular body. Because the opening in the tubular body in which the land of the closure member is fitted is of a tapered shape, air is prevented from entering and remaining in the opening when the closure member is deformed. Accordingly, when the blood pressure measuring system is primed, air is prevented from being trapped in the flow control device. As a result, the accuracy with which blood pressures are measured is increased, the flow control device can easily be de-aired, and the efficiency of blood measuring operation is highly improved. The land of the tubular body has an orifice defined by a thin wire and serving as a low-rate flow passage. The orifice is formed by the wire extending through side core pins at the same time that the tubular body is molded by injection molding. Consequently, the manufacturing process for the tubular body is simplified, and the production efficiency is increased.

Since the orifice is defined in the tubular body itself when it is molded, the manufacturing process of the invention is simpler than a conventional process in which an orifice is defined in another cylindrical member and this cylindrical member is bonded to the tubular body. Inasmuch any cylindrical member is not bonded to the tubular body and hence no adhesive is used according to the present invention, no adhesive is extracted from the tubular body. If the other cylindrical member were bonded to the tubular body, air bubbles would tend to be trapped in small surface irregularities between the cylindrical member and the tubular body. According to the present invention, since the tubular body itself has an orifice, no surface irregularities are formed by the tubular body and no air bubbles are trapped thereby. Even if air bubbles remain trapped by the tubular body, they can easily be removed. The wire for forming the orifice is of a uniform diameter. As a consequence, the orifice serving as the low-rate flow passage is uniformized in diameter. The flow control device of the present invention is less costly to manufacture as it is simple in structure and made up of a reduced number of components.

Although certain preferred embodiments have been shown and described, it should be understood that many changes and modifications may be made therein without departing from the scope of the appended claims.

What is claimed is:

1. A tubular body for reducing the rate at which a fluid flows to a predetermined rate with a resistance in a flow control device of a pressure measuring system, said tubular body comprising:
   a tubular member having an axis along which the fluid can flow therethrough and inlet and outlet passages defined in said tubular member and spaced along said axis; and
   a land projecting radially inwardly from an inner wall surface of said tubular member, said land having two slanted surfaces converging toward each other respectively from said inlet and outlet passages;
   said tubular member and said land being integrally formed as a unitary structure, said land having an orifice opening at said slanted surfaces and extending along said axis.

2. A tubular body according to claim 1, wherein said land has a flat surface positioned between the converging slanted surfaces, said flat surface partly defining a flushing passage through said tubular member.

3. A tubular body according to claim 1, wherein each of said slanted surfaces is inclined to said axis at an angle of about 5° to about 70°.

4. A tubular body according to claim 3, wherein said angle is about 10° to about 45°.

5. A tubular body according to claim 3, wherein said angle is substantially 18°.

6. A tubular body according to claim 1, wherein said tubular member and said land are made of a hard synthetic resin.

7. A tubular body according to claim 6, wherein said hard synthetic resin is polycarbonate.

8. A flow control device for use in a pressure measuring system, comprising:
   a tubular body having an inlet passage and an outlet passage which are spaced from each other along an axis of said tubular body, and including a first land having an orifice defined therein for providing communication between said inlet and outlet passages at all times; and
   an elastically deformable closure member having a second land normally held against said first land, said second land having slanted surfaces converging toward each other respectively from said inlet and outlet passages, whereby said closure member can be elastically deformed to space at least a portion of said second land from said first land to define therebetween a flow passage for allowing a fluid to pass therethrough at a relatively high rate.

9. A flow control device according to claim 8, wherein said first land projects inwardly from a side wall of said tubular body, said closure member being fitted over said tubular body, said second land projecting into said tubular body and being movable into and out of contact with said first land, whereby said closure member can be elastically deformed to permit communication between said inlet and outlet passages through said flow passage.

10. A flow control device according to claim 8, wherein said closure member has a pull knob projecting away from said second land.

11. A flow control device according to claim 8, wherein said second land has a flat surface positioned between said converging slanted surfaces, said flat surface being normally held against a flat surface of said first land to close said flow passage.

12. A flow control device according to claim 11, wherein said second land comprises a first portion including said flat surface and a second portion, and wherein said first portion is harder than said second portion.

13. A flow control device according to claim 11, further including a member having said flat surface and mounted on said second land.

14. A flow control device according to claim 8, wherein each of said slanted surfaces is inclined to said axis at an angle of about 5° to about 70°.

15. A flow control device according to claim 14, wherein said angle is about 10° to about 45°.

16. A flow control device according to claim 14, wherein said angle is substantially 24°.

17. A flow control device according to claim 8, wherein said closure member is made of an elastomeric material.

18. A flow control device according to claim 17, wherein said elastomeric material is silicone rubber.

* * * * *

UNITED STATES PATENT AND TRADEMARK OFFICE
CERTIFICATE OF CORRECTION

PATENT NO. : 5,092,561

DATED : March 3, 1992

INVENTOR(S) : MORIUCHI et al

It is certified that error appears in the above-identified patent and that said Letters Patent is hereby corrected as shown below:

Column 2, line 34, replace "prim in" with --priming--.

Column 5, line 27, replace "sup ported" with --supported--.

Column 7, lines 25-26, following the words "is slidably", insert --fitted. As shown in FIG.4, the side core pin 82 has a circular--.

Column 10, line 13, replace "fat" with --flat--.

Signed and Sealed this

Seventh Day of September, 1993

Attest:

BRUCE LEHMAN

Attesting Officer     Commissioner of Patents and Trademarks